US009528992B2

(12) United States Patent
Murauski (10) Patent No.: US 9,528,992 B2
(45) Date of Patent: Dec. 27, 2016

(54) METHODS AND KITS FOR DETECTION OF ACTIVE MALIGNANCY (71) Applicant: Uladzimir A. Murauski, Berlin (DE)

(72) Inventor: Uladzimir A. Murauski, Berlin (DE)

(*) Notice: Subject to any disclaimer, the term of this patent is extended or adjusted under 35 U.S.C. 154(b) by 105 days.

(21) Appl. No.: 14/380,032

(22) PCT Filed: Feb. 20, 2013

(86) PCT No.: PCT/EP2013/053389
§ 371 (c)(1),
(2) Date: Aug. 20, 2014

(87) PCT Pub. No.: WO2013/124325
PCT Pub. Date: Aug. 29, 2013

(65) Prior Publication Data
US 2015/0037907 A1    Feb. 5, 2015

Related U.S. Application Data (60) Provisional application No. 61/600,944, filed on Feb. 20, 2012.

(51) Int. Cl.
G01N 31/00    (2006.01)
G01N 33/53    (2006.01)
G01N 33/574   (2006.01)

(52) U.S. Cl.
CPC .. G01N 33/57434 (2013.01); G01N 33/57415 (2013.01); G01N 33/57419 (2013.01); G01N 33/57488 (2013.01); G01N 2333/765 (2013.01)

(58) Field of Classification Search
CPC .................. G01N 33/6893; G01N 2800/26
See application file for complete search history.

(56) References Cited

U.S. PATENT DOCUMENTS

| 5,183,740 | A | 2/1993 | Ligler et al. |
| 5,308,604 | A | 5/1994 | Sinn et al. |
| 6,306,576 | B1 | 10/2001 | Hazen et al. |
| 6,458,758 | B1 | 10/2002 | Hsia |
| 6,589,751 | B2 | 7/2003 | Ferguson et al. |
| 6,989,369 | B2 | 1/2006 | Ladner et al. |
| 7,060,292 | B2 | 6/2006 | Melchior et al. |
| 7,070,937 | B1 | 7/2006 | Bar-Or et al. |
| 7,166,474 | B2 | 1/2007 | Muravsky et al. |
| 7,172,873 | B2 | 2/2007 | McDonald et al. |
| 7,238,667 | B2 | 7/2007 | Rosen et al. |
| 8,632,986 | B2 * | 1/2014 | Murauski ........... G01N 33/6893 422/430 |
| 2003/0143191 | A1 | 7/2003 | Bell et al. |
| 2003/0170912 | A1 | 9/2003 | Muravsky et al. |
| 2006/0122374 | A1 | 6/2006 | Mertins et al. |
| 2007/0231847 | A1 | 10/2007 | Bar-Or et al. |
| 2007/0275483 | A1 | 11/2007 | Liotta et al. |

FOREIGN PATENT DOCUMENTS

| EP | 0973043 | 1/2000 |
| SU | 1459656 | 2/1989 |
| WO | 9420863 | 9/1994 |
| WO | 2007041596 | 4/2007 |
| WO | 2007079886 | 7/2007 |
| WO | 2010049010 | 5/2010 |
| WO | WO 2010/049010 A1 * | 5/2010 ............. G01N 33/68 |

OTHER PUBLICATIONS

Altamentova et al. A fluorescence method for estimation of toxemia: Binding capacity of lipoproteins and albumin in plasma. Clinica Chimca Acta. 271(2). 133-149. 1998.
Caldararu et al. A spin probe study of mesoporous silica formation via a neutral templating route. Journal of Physical Chemistry Part B: Condensed Matter, Materials, Surfaces, Interfaces & Biophysical. 107(25):6032-6038. 2003.
Gurachevsky et al. Application of spin label electron paramagnetic resonance in the diagnosis and prognosis of cancer and sepsis. Clin. Chem. Lab Med. 2008. vol. 46. No. 9. pp. 1203-1210. 2008.
Office Communication. Issued in European Application No. 08 875 351.2. Mailed on Mar. 30, 2012.
PCT International Preliminary Report on Patentability issued in International application No. PCT/EP2008/066030. Dated May 3, 2011.
PCT International Search Report issued in International application No. PCT/EP2008/066030. Dated Jul. 3, 2009.
Smirnova. Binding of MRI contrast agents to albumin: A high-field EPR study. Applied Magnetic Resonance. 31 (3-4). 431-446. 2007.
Office Communication. Issued in European Application No. 08 875 351.2. Dated Feb. 4, 2011.
International Search Report and Written Opinion issued in PCT/EP2013/053389, mailed Jun. 13, 2013.
Gelos et al., "Analysis of albumin fatty acid binding capacity in patients with benign and malignant colorectal diseases using electron spin resonance (ESR) spectroscopy", International Journal of colorectal Disease, 25(1):119-127, 2009.
Schneider et al., "Calculating Slow Motional Magnetic Resonace Spectra, A User's Guide", Biological Magnetic Resonance, vol. 8, 1989.

* cited by examiner

Primary Examiner — Lisa Cook

(57) ABSTRACT

Various embodiments of methods and kits are disclosed for detection and/or diagnosis of cancer (e.g., active malignancy) in a subject patient by analyzing a first sample of the subject patient's albumin-containing extracellular fluid (e.g., blood serum). Some embodiments comprise analyzing a second sample of the subject patient's albumin-containing extracellular fluid obtained between 2 and 90 days (e.g., between 5 and 30 days) after the first sample.

19 Claims, 4 Drawing Sheets a) 16-DOXYL-stearic acid, free radical
   Distributors: TCI; Flurochem; Sigma-Aldrich b) 5-DOXYL-stearic acid, free radical
   Distributor: Sigma-Aldrich c) 16:0-16 PC DOXYL, free radical (1-Palmitoyl-2-Stearoyl-(16-DOXYL)-sn-Glycero-3-Phosphocholine)
   Producer and distributor: Avanti Polar Lipids Inc.

FIG. 1A d) 12-N-Methyl-7-nitrobenzo-2-oxa-1,3-diazolamino stearate [12-NBDS or NBD-stearate], fluorescent probe (Fluorescent labeled stearic acid). CAS Registry: 117056-67-4 e) 12-(9-anthroyl)stearic acid [ anthroylstearic acid ], fluorescent probe (Fluorescent labeled stearic acid). CAS Registry: 37469-99-1

1) Pipetting of a stock solution of the probe into a well of a plate following by a drying of the well
2) Pipetting of serum into the well
3) Pipetting of a polar solvent into the well
4) Filling up a capillary tube with the sample
5) Measurement of ESR spectrum for the capillary
6) Spectra processing and result calculation

FIG. 3

METHODS AND KITS FOR DETECTION OF ACTIVE MALIGNANCY

This application is a national phase application under 35 U.S.C. §371 of International Application No. PCT/EP2013/053389, filed Feb. 20, 2013, which claims the benefit of U.S. Provisional Patent Application Ser. No. 61/600,944, filed Feb. 20, 2012 the contents of which applications are incorporated by reference in their respective entireties.

BACKGROUND

1. Field of the Invention

The present invention relates generally to analysis of extracellular fluids that contain carrier proteins (e.g., serum albumin), and, more particularly, but not by way of limitation, to methods for prognosis and detection of active (e.g., aggressive) malignancy in a patient by analyzing serum or plasma samples from the patient.

2. Description of Related Art

For illustration, but without limiting the scope of the invention, the background is described with respect to analyzing the blood of a human patient.

In the patient with active cancer, malignant cells may grow aggressively, forming and growing malignant cells and invading parts of the body near an initial tumor during early stages, and spreading to more distant parts of the body through the blood stream and/or lymphatic system during later stages. These processes are often accompanied by secretion of multiple metabolites to the circulatory system of the patient.

Analyzing hematologic parameters and/or measuring the concentration of various metabolites in blood samples from a patient are known in the art and may be widely-used methods of diagnosing cancer in a patient, such as, for example, by identification of antigens, hormones, enzymes and other biologically active substances (tumor markers).

Currently known tumor markers are generally each useful for diagnosing a certain type of cancer, such as, for example, alpha-fetoprotein for liver cancer, human chorionic gonadotropin (HCG) for some types of testicular and ovarian cancer, prostate-specific antigen for prostate cancer, CA 15-3 for breast cancer, and several others. These tumor markers may not permit recognition or diagnosis of active cancer until later stages when other symptoms are already noticeable and the patient is investigated with methods such as X-rays, CT scans, endoscopy and biopsy. In these later stages, treatment may be less effective and may not be effective enough to prevent the death of the patient.

One example of a known method may be referred to in the art as "mass spectrometry-based profiling" of metabolites residing in extracellular fluids (also known as Metabonomics), such as, for example, profiling of low molecular mass serum proteins (Proteomics) and peptides (Peptidome). Certain studies have indicated that, in a patient with any of several types of types of active malignancy, mass-spectrometry based profiling may detect significant changes in profiles of low-molecular mass metabolites in serum and other extracellular fluids. These changes appear to be caused by (i) infusion of specific metabolites produced by cancer cells, (ii) disturbance of normal metabolic processes resulting from mediators, intermediates and other bio-active molecules secreted by tumor cells, and/or (iii) acute-phase response metabolites produced by tissue invaded by malignant cells. Certain of these studies also discovered that low-molecular weight metabolites (e.g., peptide fragments) that may be generated as a consequence of the disease process, are often immediately bound to high-abundance carrier proteins (e.g., albumin), and thereby prevented from being cleared from the patient's blood by the liver.

Serum albumin is generally the most abundant serum protein, and provides a primary transport of hydrophobic metabolites in the circulatory system of the organism. The structure of the albumin molecule includes three domains that, in the hydrophilic medium of blood, are generally folded in an albumin globule of a heart-like and/or ellipsoidal shape in which hydrophilic binding sites generally face outward, and the hydrophobic binding sites generally face inward to form what may be referred to as one or more "hydrophobic containers" or "hydrophobic cavities" in the interior of the globule. The albumin molecule has multiple specific and non-specific hydrophobic sites which bind various long-chain fatty acids and other hydrophobic metabolites. In the albumin-bound state, hydrophobic metabolites are transferred and/or accumulated in hydrophilic extracellular fluids in the body.

Known techniques of profiling of serum metabolites generally require dissociation of all albumin-bound metabolites, which may cause a number of shortcomings and/or drawbacks. Additionally, known techniques for profiling of serum metabolites generally are as a research tool for discovery of new tumor biomarkers, rather than as a diagnostic tool for diagnosing cancer.

European Patent Application, EP 0 973 043 A1, published Jan. 19, 2000, describes a method of diagnosing malignant neoplasms by using electron paramagnetic resonance (EPR) spectroscopy (which may also be known in the art as electron spin resonance "ESR" spectroscopy), wherein an aliquot of a subject patient's serum is mixed with the spin probe represented by spin labeled fatty acid. In this method, a malignant disease is detected based upon the deviation of physicochemical parameters of the mobility of the spin probe in three binding sites of serum albumin, relative to values exhibited in healthy subjects. This method may produce false-positive and false-negative results in the presence of additional factors such us evaluated blood lipid values, injection of medicaments, elevated blood alcohol level, residing infection diseases of the subject patient, as well effects caused by a solvent of the spin probe.

U.S. Pat. No. 7,166,474 describes a method of detecting changes in transport properties of albumin by using electron paramagnetic resonance (EPR) spectroscopy (which may also be known in the art as electron spin resonance "ESR" spectroscopy) to evaluate a sample that contains albumin (an albumin-containing sample). This method can include evaluating the albumin transport function with respect to long chain fatty acids by using a spin probe represented by a spin-labeled fatty acid. Specifically, according to this method, the EPR-spectra of the spin probe can be measured in at least three aliquots of the sample, where each aliquot is mixed with significantly different concentrations of the spin probe and a high concentration of ethanol. The concentration of ethanol is high enough to induce significant conformational changes of the albumin to enable evaluation of the conformational flexibility of the albumin. The conformational state and binding parameters of the albumin are determined from the parameters of the spin probe mobility in two binding sites of serum albumin, and the concentration of unbound spin probe. The parameters of albumin transport function are derived from measurements of the conformational changes induced in the albumin artificially by the high ethanol concentration. This method assumes that albumin molecules efficiently release bound substances to target objects at conditions that occur in a healthy patient, and therefore induces a conformational change facilitating dissociation of albumin-bound metabolites.

This method can include detection of cancer via the evaluation of the conformational changes of albumin in respect of modification caused by metabolites associated with a tumor growth. While this may be useful in the method taught by this patent, the conformational changes of albumin molecules induced by the high ethanol concentration cause dissociation of a significant portion of albumin-bound spin probe in the investigated sample, which largely prevents correct evaluation of the albumin conformation. For example, due to their hydrophobic origin, spin probe molecules dissociated from albumin will aggregate into micelles and associate with or bind to serum lipoproteins. During the measurements of EPR spectrum, these dissociated portions of spin probe (aggregated into micelles and associated with or bound to serum lipoproteins) can induce EPR signals that interfere with those from the spin probe bound on albumin sites, and thereby prevent precise evaluation of the albumin conformation.

This method suffers from possible shortcomings that may include, for example, the use of at least three aliquots of each sample, binding on albumin of acute-phase response metabolites in early (e.g., asymptomatic) stages of infection or disease, and excessive dissociation of spin probe from the albumin (and resulting spin probe aggregation into micelles and binding to serum lipoproteins) resulting from the addition of relatively high-concentrations of ethanol. These possible shortcomings may, in some instances, contribute to variations in results, including false-positives and false-negatives in detecting the presence of metabolites associated with an active malignant growth in a patient.

SUMMARY

Various embodiments of the present invention can be suitable for detecting variations in serum albumin conformation, functions, characteristics, and/or parameters by mixing various substances with a sample of extracellular fluid (that contains (e.g., serum albumin)) from a subject patients, and analyzing the mixture. Examples of such extracellular fluids include blood serum, blood plasma, lymph fluid, and spinal fluid. Some embodiments of the present methods are suitable for prognosis (predicting the onset of), detection, or diagnosis of active malignancy in its early or precursor stages. The present invention may be suitable, for example, for diagnosis and/or monitoring of cancer patients in clinical settings. By way of further examples, the present invention may be suitable for such diagnosis, prognosis, monitoring, and/or relapse detection of cancer patients after treatment, or patients (e.g., chemotherapy, radiotherapy, and/or the like).

In some embodiments, the methods of the present invention can be suitable for detection, diagnosis, or prognosis of active malignancy, by detecting or measuring the deviation of parameters of spin probe binding to serum albumin of a subject patient, relative to the parameters of spin probe binding to serum albumin of a control patient. The probe binding parameters of the control patient can be established, for example, by testing one or more control patients, by historical test results from patients with known conditions, by statistical aggregation of data from various other patients, or by any other suitable means that permits comparison with the subject patient in such a way as to provide an indication of whether the subject patient has, likely has, is likely to have, does not have, likely does not have, or is not likely to have active malignancy. This deviation can, for example, be detected or measured for a sample of serum taken from a subject patient by mixing an aliquot of the serum sample with a labeled hydrophobic probe having a long-hydrocarbon-chain. Specifically, parameters of binding of a hydrophobic probe having a long-hydrocarbon chain to serum albumin can correlate to the amount of cancer-associated metabolites bound to the binding sites of the albumin. This correlation can, for example, be caused by competitive binding on specific albumin sites for substances with long hydrocarbon chains, and indirectly due to allosteric modification of the conformation and affinity of these sites upon ligand binding on other albumin sites. Stated otherwise, when high levels of cancer-associated metabolites are present in the subject patient's blood, these metabolites may crowd and/or modify the binding sites of the serum albumin, thereby preventing the hydrophobic probe from binding to those binding sites. In this way, metabolites associated with active malignant growth can be detected as their levels rise, and even before other sign or symptoms of the cancer appear.

The present invention includes various embodiments of methods for detecting active malignancy in a subject patient. Some embodiments of the present methods (e.g., for detecting active malignancy in a subject patient) comprise: obtaining a first sample of a subject patient's serum albumin-containing extracellular fluid; mixing a labeled hydrophobic probe capable of binding to serum albumin with an aliquot of the first sample, the amount of probe such that the molar ratio of the probe to the serum albumin is between about 2 and about 7, the probe optionally comprising two or more substances; mixing a solvent with the aliquot of the first sample, the solvent such that when added to the aliquot and probe the solubility of the probe is increased in the aliquot, and the amount of solvent is sufficient to dissociate a portion of the probe from the serum albumin without causing significant dissociation of hydrophobic metabolites from the serum albumin, the solvent optionally comprising two or more substances; analyzing the mixture of aliquot, probe, and solvent to determine for the first sample one or more binding parameters of the probe; and comparing the one or more binding parameters of the first sample to one or more control binding parameters of a probe binding to serum albumin in the extracellular fluid of at least one of: a cancer-free control patient and a control patient with an active malignancy. Some embodiments further comprise: obtaining a second sample of the subject patient's serum albumin-containing extracellular fluid taken from the subject patient between 2 and 90 days after the first sample; mixing a labeled hydrophobic probe capable of binding to serum albumin with an aliquot of the second sample, the amount of probe such that the molar ratio of the probe to the serum albumin is between about 2 and about 7, the probe optionally comprising two or more substances; mixing a solvent with the aliquot of the second sample, the solvent such that when added to the aliquot and probe the solubility of the probe is increased in the aliquot, and the amount of solvent is sufficient to dissociate a portion of the probe from the serum albumin without causing significant dissociation of hydrophobic metabolites from the serum albumin, the solvent optionally comprising two or more substances; analyzing the mixture of aliquot, probe, and solvent to determine for the second sample one or more binding parameters of the probe; and comparing the one or more binding parameters of the second sample to one or more control binding parameters of a probe binding to serum albumin in the extracellular fluid of at least one of: a cancer-free control patient and a control patient with an active malignancy.

Some embodiments of the present methods (e.g., for detecting active malignancy in a subject patient) comprising: obtaining two samples of a subject patient's serum albumin-containing extracellular fluid taken from the subject patient between 2 and 90 days apart; mixing a labeled hydrophobic probe capable of binding to serum albumin with an aliquot of each sample, the amount of probe such that the molar ratio of the probe to the serum albumin is between about 2 and about 7, the probe optionally comprising two or more substances; mixing a solvent with the aliquot of each sample, the solvent such that when added to the aliquot and probe the solubility of the probe is increased in the aliquot, and the amount of solvent is sufficient to dissociate a portion of the probe from the serum albumin without causing significant dissociation of hydrophobic metabolites from the serum albumin, the solvent optionally comprising two or more substances; analyzing each mixture of aliquot, probe, and solvent to determine for each sample one or more binding parameters of the probe; and comparing the one or more binding parameters of each sample to one or more control binding parameters of a probe binding to serum albumin in the extracellular fluid of at least one of: a cancer-free control patient and a control patient with an active malignancy.

Some embodiments of the present methods further comprise: diagnosing an active malignancy in the subject patient if: (i) the one or more binding parameters for each of the two samples are closer to the one or more control binding parameters for the at least one control patient with an active malignancy than to the one or more control binding parameters of the cancer-free control patient, and (ii) the subject patient had no indication of acute disease or infection that occurred between the times of the deriving of the samples. In some embodiments, the labeled hydrophobic probe is capable of binding to specific and non-specific hydrophobic binding sites of serum albumin. In some embodiments, analyzing each mixture comprises: substantially excluding from the mixture a portion of the probe that is bound on lipoproteins and a portion of the probe that is aggregated into micelles; and determining the one or more probe binding parameters of the sample from the remaining portion of the probe in the mixture. In some embodiments, the one or more probe binding parameters of each sample are determined from the portion of the probe bound to specific and non-specific hydrophobic binding sites of albumin, and the portion of unbound probe. In some embodiments, the two samples are taken from the subject patient between 5 and 90 days apart, between 2 and 30 days apart, or between 5 and 30 days apart.

Some embodiments of the present methods further comprise: verifying that the subject patient had no indication of acute diseases that occurred between the times at which the two samples were taken from the patient. In some embodiments, analyzing each mixture comprises: measuring the concentrations of the probe bound on specific and non-specific hydrophobic sites of serum albumin, and the unbound probe in the mixture; and deriving the one or more probe binding parameters from at least the concentrations of: the probe bound to specific and non-specific hydrophobic binding sites of albumin, and the unbound probe. In some embodiments, the probe comprises an organic molecule having between 8 and 28 Carbon atoms, and optionally, where the probe comprises one or more of: a fatty acid, a long-chain fatty acid, 16-DOXYL-stearic acid, or a lysophospholipid. In some embodiments, the amount of solvent mixed with the aliquot and probe is such that the solvent does not induce significant conformational changes of albumin. In some embodiments, the amount of solvent mixed with the aliquot and probe is sufficient to increase the concentration of unbound probe in the mixture of the aliquot, the probe, and the solvent to at least 5 times greater than the concentration of unbound probe in a mixture of the aliquot and the probe without the solvent. In some embodiments, the volume of the solvent mixed with the aliquot is less than about 30% of the volume of the aliquot, and optionally less than about 20% of the volume of the aliquot.

Some embodiments of the present methods further comprise: normalizing the one or more probe binding parameters of each sample to account for the reduction in albumin concentration caused by the solvent in the mixture; and optionally, where the steps of deriving and normalizing the one or more probe binding parameters are performed simultaneously. Some embodiments comprise: normalizing the one or more probe binding parameters of each sample to account for the reduction in serum albumin concentration caused by medical conditions of the patient. In some embodiments, the one or more control parameters comprise at least one range of control parameters of control patients. Some embodiments comprise: repeating the steps of mixing a probe, mixing a solvent, measuring the concentrations, deriving a one or more probe binding parameters for each of two or more aliquots, where a different amount of solvent is used for each of the two or more repetitions; optionally, where the one or more probe binding parameters derived for the two or more repetitions are averaged to derive an average probe binding parameters, and where the averaged one or more probe binding parameters are compared in the step of comparing the one or more probe binding parameters.

In some embodiments of the present methods, the volume of the aliquot is less than about 100 μL, and optionally, less than about 50 μL. In some embodiments, the probe is labeled with a spin-label. In some embodiments, the extracellular fluid includes at least one of: blood serum, blood plasma, lymph fluid, and spinal fluid. In some embodiments, analyzing each mixture comprises verifying that the mixture has reached binding equilibrium, optionally by: measuring two EPR spectra of the mixture at two different times; and comparing the two EPR spectra to determine whether intensities of spectral lines (spectral parameters) in the EPR spectra correspond.

Some embodiments of the present kits (e.g., for detecting active malignancy in a subject patient from a sample of the subject patient's serum albumin-containing extracellular fluid) comprise: a labeled hydrophobic probe capable of binding to specific and non-specific hydrophobic binding sites of serum albumin, the amount of probe such that when mixed with an aliquot having a predetermined volume of the extracellular fluid, the molar ratio of the probe to the carrier proteins is in the range of about 3 to about 4; and a solvent, the solvent configured such that when mixed with the probe and the aliquot the solubility of the probe is increased in the aliquot, and the amount of solvent sufficient to dissociate a portion of the probe from the albumin without causing significant dissociation of hydrophobic metabolites from serum albumin.

Some embodiments of the present kits further comprise instructions for: mixing a labeled hydrophobic probe capable of binding to specific and non-specific hydrophobic binding sites of serum albumin with an aliquot having a predetermined volume of a subject patient's extracellular fluid containing serum albumin, the amount of probe such that the molar ratio of the probe to the carrier proteins is between about 3 and about 4; and mixing an amount of solvent with the mixture of the probe and the aliquot sufficient to dissociate a portion of the probe from the carrier proteins without causing significant dissociation of hydrophobic metabolites from serum albumin. Some embodiments comprise instructions for: analyzing the mixture of the aliquot, probe, and solvent to determine one or more binding parameters of the probe; and comparing the one or more binding parameters of each sample to one or more control binding parameters of a probe binding to serum albumin in the extracellular fluid of at least one of: a cancer-free control patient and a control patient with an active malignancy. In some embodiments, instructions for analyzing the mixture comprise instructions for: substantially excluding from the mixture a portion of the probe that is bound on lipoproteins and a portion of the probe that is aggregated into micelles; and determining the one or more probe binding parameters of the sample from the remaining portion of the probe in the mixture. In some embodiments, the instructions for analyzing the mixture comprise instructions for: measuring the concentrations of the probe bound on specific and non-specific hydrophobic sites of serum albumin, and the unbound probe in the mixture; and deriving the one or more probe binding parameters from at least the concentrations of: the probe bound to specific and non-specific hydrophobic binding sites of albumin, and the unbound probe.

Any embodiment of any of the present methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those steps. Likewise, a step of a method that "comprises," "has," "includes" or "contains" one or more features possesses those one or more features, but is not limited to possessing only those one or more features. For example, in a method that comprises the step of obtaining a sample of blood serum containing serum albumin, the blood serum includes the specified features but is not limited to having only those features. For example, in such a method, the blood serum could also contain water.

Further, a device or structure that is configured in a certain way is configured in at least that way, but it can also be configured in other ways than those specifically described.

Various embodiments of the present methods may include testing, analyzing, and/or evaluating of a sample of extracellular fluid from a subject patient. For clarity and brevity, embodiments are described below for testing blood serum of a subject patient. However, the embodiments, features, steps, and particulars described below can also be applied to other extracellular fluids such as, for example, blood plasma, lymph fluid, spinal fluid, and the like.

Some embodiments of the present methods include obtaining a serum sample from a subject patient. A serum sample can be obtained, for example, by drawing blood from the patient and using centrifugation to substantially isolate the serum from the blood. Other suitable methods may also be used to obtain the serum sample from the subject patient. An aliquot can also be obtained from this subject sample. Such an aliquot can be separated from the sample or can include the entire sample.

Some embodiments of the present method include mixing a labeled hydrophobic probe with the aliquot. The labeled hydrophobic probe may also be referred to herein as the "labeled probe," the "hydrophobic probe," or the "probe." The probe is (or comprises) an organic molecule, and/or is selected to be capable of binding with albumin of the serum in an aliquot of a serum sample from a patient. In some embodiments, the probe can comprise a suitable number of Carbon atoms. For example, the probe can comprise between 8 and 28 Carbon atoms, including 8, 9, 10, 11, 12, 13, 14, 15, 16, 17, 18, 19, 20, 21, 22, 23, 24, 25, 26, 27, or 28 Carbon atoms, or any smaller range between 8 and 28 Carbon atoms, e.g., between 14 and 22, between 16 and 20, or between 18 and 22 Carbon atoms. In another example, the probe can comprise less than 8 Carbon atoms or more than 28 Carbon atoms. In some embodiments, the probe can comprise a hydrocarbon chain such as, for example, a hydrocarbon chain having any suitable number of Carbon atoms. In some embodiments, the probe can comprise a hydrocarbon molecule whose structure is branched and/or whose structure comprises a ring structure. In some embodiments, the probe can comprise a hydrocarbon molecule comprising elements other than Carbon or Hydrogen, such as, for example, Chlorine, Phosphorous, and/or Nitrogen.

In some embodiments, the probe can comprise a hydrocarbon chain such as, for example, a fatty acid, a long-chain fatty acid, a medium-chain fatty acid, or the like. Examples of probes suitable for some embodiments of the present method include: 16-DOXYL-stearic acid, free radical; 5-DOXYL-stearic acid, free radical; 16:0-16 PC DOXYL, free radical (1-Palmitoyl-2-Stearoyl-(16-DOXYL)-sn-Glycero-3-Phosphocholine); 12-NBDS or NBD-stearate, fluorescent probe (12-N-Methyl-7-nitrobenzo-2-oxa-1,3-diazolamino stearate); and anthroylstearic acid, fluorescent probe (12-(9-anthroyl)stearic acid). Such labeled probes are available from commercial suppliers including, for example, (1) Sigma-Aldrich, Inc., St. Louis, Mo., U.S.A., www.sigmaaldrich.com; (2) TCI America, Portland, Oreg., U.S.A. and Wellesley Hills, Mass., U.S.A, www.tciamerica.com; (3) Fluorochem, Derbyshire, U.K., www.fluorochem.co.uk; (4) Avanti Polar Lipids Inc., Alabaster, Ala., U.S.A., www.avantilipids.com; and (5) Santa Cruz Biotechnology, Inc., Santa Cruz, Calif., U.S.A., http://www.scbt.com.

In some embodiments, the probe may be suspended in a volume of liquid so as to, for example, enable accurate measurement of the amount of the probe. This liquid is referred to herein as the "suspension liquid" or "liquid" so as not to be confused with the solvent described herein (even though the suspension liquid may be or comprise a solvent as that term is used in a more general sense). In some of these embodiments, the suspension liquid may be (or comprise) the solvent, which is described below. In some of these embodiments, the probe may be suspended in the solvent in an amount desired for mixing the aliquot, probe, and solvent without further addition of solvent; or may be suspended in an amount of solvent smaller than is desired, such that additional solvent must be separately added to the mixture. For example, if 10 µL of solvent are mixed with a 50 µL aliquot: (1) the probe may be suspended in 10 µL of solvent and the suspension added to the aliquot; or (2) the probe may be suspended in 5 µL of solvent, the suspension added to the aliquot, and 5 µL of solvent (without probe) also mixed with the aliquot. Examples of suitable solution liquids, for use where the probe solution and solvent are mixed while both are liquid, include the materials described below for the solvent.

In others of these embodiments (in which the probe may be suspended in a volume of liquid), the probe solution may be added to a container first and the liquid portion of the liquid/probe solution permitted to evaporate, leaving substantially-only the probe in the container. In such embodiments, the aliquot of serum may then be added such that the probe then dissolves into the serum. Examples of suitable liquids for this suspension/evaporation method include both the liquids described below for the solvent, as well as other liquids (including solvents known in the art as non-polar solvents) that are not miscible with water, such as, for example, methyl ethyl ketone, methyl acetate, diethyl ether, dichloro methane, benzene, pentane, cyclo pentane, etc.

In some embodiments, the amount of probe mixed with the aliquot is sufficient to permit a representative level of binding of the probe to the specific (primary) and non-specific (secondary) hydrophobic sites of serum albumin, i.e., a level of binding that is sufficient to be representative of the probe binding to the specific and non-specific hydrophobic sites, respectively, of serum albumin in the subject patient's body at the time the sample was taken from the subject patient. In some embodiments, the amount of probe is also small enough to prevent (or to not permit) saturation of the fatty acid binding sites on the serum albumin. In some embodiments, the amount of probe is such that the molar ratio of probe (that is capable of binding with specific and non-specific sites of serum albumin) to the serum albumin is between about 3 and about 5 so as to, for example, encourage binding of the probe to albumin in a manner that is representative of the circulatory system of the patient. In some embodiments, the molar ratio of the probe to the serum albumin is greater than, less then, or between any of about 1, 2, 3, 4, 5, 6, or 7. In other embodiments, the molar ratio of the probe concentration to the serum albumin concentration can be any suitable ratio that permits the present methods to function as described.

The concentration of serum albumin in the serum can be approximated from various texts known in the art. In some embodiments, the concentration of serum albumin can be approximated as the expected concentration of serum albumin in a healthy patient. In such embodiments, results can later be adjusted (as described below) to account for any reduction in albumin concentration expected as a result of the medical conditions of the patient (e.g., toxemia). In some embodiments, the concentration of serum albumin can be approximated as the expected concentration of serum albumin in a patient with the same medical conditions of the subject patient (e.g., active cancer, tumor remission stage, post-surgery and/or the like), and the amount of probe adjusted accordingly so as to, for example, reduce or eliminate the need to adjust results later to account for a reduction in serum albumin concentration caused by medical conditions of a subject patient.

Some embodiments of the present method include mixing a solvent with the aliquot to, for example, increase the solubility of the hydrophobic probe in the hydrophilic medium of the aliquot. As used specifically herein, the "solvent" mixed with the aliquot is a substance (or combination of substances) capable of increasing the solubility of the probe in the mixture (of at least aliquot, probe, and solvent), and can comprise one or more substances generally known in the art as solvents (e.g., polar solvents) and/or one or more substances not generally considered to be solvents (e.g., solids, water-based or other solutions, and the like). In some embodiments, the solvent may include a mixture of two or more substances. In some embodiments, the solvent is selected to be capable of causing some dissociation of the probe from the serum albumin in the aliquot. In some embodiments, the solvent can be (or comprise) a liquid that is miscible with, or soluble in, water (and/or that may be known in the art as a polar solvent), such as, for example, methanol, ethanol, acetonitrile, dimethyl sulfoxide DMSO), tetrahydrofuran (THF), acetic acid, formamide, and the like. In some embodiments, the solvent may be added at any suitable stage or in any suitable manner, including, for example, to the aliquot alone, to the probe alone, to a mixture of only the aliquot and probe, or to the complete mixture of aliquot, probe, and solvent.

Some embodiments of the present methods include mixing water with any component of the mixture or the entire mixture at any suitable stage, including, for example, to the aliquot alone, to the probe alone, to a mixture of only the aliquot and probe, or to the complete mixture of aliquot, probe, and solvent. Some embodiments of the present methods include mixing additives with the water, with the solvent described above, with any other component of the mixture, and/or or with the complete mixture, to adjust or modify the isotonic properties of the sample mixture. For example, some embodiments of the present method include mixing an amount of NaCl with water to achieve a concentration of about 0.9% NaCl to simulate the isotonic properties of blood and the normal cells of the body, as may be done in other areas of medicine and biological sciences.

In some embodiments where the solvent is selected to be capable of causing dissociation of the probe from serum albumin, the amount of solvent added to the aliquot is such that a portion of the probe is dissociated from (caused to not bind or stop binding with) the serum albumin without causing significant dissociation of hydrophobic metabolites from the serum albumin. As used here, "significant dissociation of toxins" is dissociation from serum albumin that substantially affects the representative nature of the binding properties exhibited by the serum albumin in the aliquot (relative to the binding properties the same serum albumin exhibited in the subject patient's body at the time the sample was obtained from the subject patient).

This lack or relatively minimal amount of dissociation of toxins may also be described as, simply, "without causing dissociation of toxins." As used here, "without causing dissociation of toxins" does not necessarily mean that no toxins are dissociated from the serum albumin, and in fact, some toxins may be dissociated from serum albumin. Instead, as used here, "without causing dissociation of toxins" means that the binding properties exhibited by the serum albumin in the aliquot are still representative of the binding properties the same serum albumin exhibited in the subject patient's body at the time the sample was obtained from the subject patient).

In such embodiments, and in contrast to U.S. Pat. No. 7,166,474 (described above in background section), the amount of solvent added to the aliquot is also such that the solvent does not induce significant conformational changes to the serum albumin. As used here, "significant conformational changes" are conformational changes to the serum albumin that significantly affect the representative nature of the albumin conformation and binding properties exhibited by the serum albumin in the aliquot (relative to the conformation and binding properties the serum albumin exhibited in the subject patient's body at the time the sample was obtained from the subject patient). For example, a conformational change would be significant if it caused the serum albumin to release bound hydrophobic metabolites so as to bind a measurably greater amount of probe than the serum albumin would have bound without such conformational changes.

In some embodiments, the amount of solvent is such that the concentration of unbound (free) probe in the mixture (of aliquot, probe, and solvent) is at least a multiple greater than (e.g., 5, 6, 7, 8, 9, 10, 20, 50, 100, 500, 1000, 5000, 10000, or 100000 times greater than) the concentration of unbound (free) probe before the addition of the solvent (e.g., in a mixture of only the aliquot and probe). In other embodiments, the amount of solvent is such that the concentration of unbound (free) probe in the mixture (of aliquot, probe, and solvent) is in a range between about a lower multiple and about a higher multiple greater than (e.g., between about 5 and about 10, between about 10 and about 100, or between about 100 and about 1000 times greater than) the concentration of unbound (free) probe before the addition of the solvent (e.g., in a mixture of only the aliquot and probe).

In some embodiments, the volume of the amount of solvent mixed with the aliquot is a percentage of the volume of the aliquot. For example, for a 50 µL aliquot, the volume of solvent added may be between about 1% and about 30%, i.e., between about 0.5 µL and about 15 µL, or in any individual percentage or range of percentages within this range, e.g., about 10%, about 20%, between about 5% and about 20%, between about 10% and about 20%, or the like. In some embodiments, the volume of solvent mixed with the aliquot is greater than about and/or less than about any of: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, and 30%. In some embodiments, a specific volume of solvent mixed with the aliquot is within this range, such as, for example, for an aliquot of 50 µL, about 1 µL, about 5 µL, about 10 µL, about 15 µL, about 20 µL, or any other suitable volume of solvent can be added.

The addition of solvents in such amounts can reduce variations and/or errors by largely overcoming the influence of stochastic factors such as, for example, influences caused by various trace substances in the aliquot. For example, an aliquot of serum may have trace amounts of alcohol that vary significantly relative to trace amounts of alcohol in a different aliquot of serum. Such significant relative differences may introduce variations that can affect the repeatability and reliability of the results achieved. By adding the solvent (in an amount to achieve the effects described above) prior to analyzing the mixture, the relative significance of such variations can be reduced. This reduction in relative significance can increase the repeatability and reliability of the results achieved by the present methods.

In some embodiments, the probe and the solvent can be mixed together prior to mixing either of the probe or solvent with the aliquot. In some embodiments, a surfactant may also be added to the mixture to promote, encourage, or assist the binding of probe to the serum albumin in the aliquot of serum. In such embodiments, the surfactant may be added at any suitable stage or in any suitable manner, including, for example, to the aliquot alone, to the probe alone, to a mixture of only the aliquot and probe, or to the complete mixture of aliquot, probe, and solvent. Examples of suitable surfactants include nonionic detergents such as Tween 20 and Triton X-100, which may be available from suppliers such as Sigma-Aldrich, Inc., St. Louis, Mo., U.S.A., www.sigmaaldrich.com. Some embodiments of the present methods may include incubating the mixture (of probe, solvent, and aliquot of serum) for a period of time including, for example, equal to, less than, or between any of about: 30, 20, 15, 10, 9, 8, 7, 6, 5, 4, 3, 2, or 1 minutes. Some embodiments of the present methods may include agitation of the mixture (e.g., by shaking, or by shaking at between, greater than, less than, or between about 5 and 8 Hz for a period of time that can be separate from or at least partially (including wholly) concurrent with the incubation, including, for example, less than about any of 30, 20, 10, 9, 8, 7, 6, 5, 4, 3, 2, or 1 minutes. Additionally, some embodiments may include incubating and/or agitating the mixture at about a predetermined temperature such as, for example, 37° C. (approximate human body temperature), room temperature (from 20 to 25° C.) or the like. In other embodiments, the mixture can be agitated and/or incubated for any suitable period of time, at any suitable frequency, and/or at any suitable temperature.

As described in more detail below, some embodiments of the present method include analyzing the mixture of the aliquot, probe, and solvent to determine the parameter of the probe binding to serum albumin including, for example, as a function of concentrations of residual-free and two fractions of the probe bound on specific (primary) and non-specific (secondary) hydrophobic sites of serum albumin in the aliquot.

In some embodiments, and in contrast to U.S. Pat. No. 7,166,474 (described above), the present methods can include analyzing two samples of a patient's albumin-containing extracellular fluid (e.g., serum) obtained at two different times (e.g., 5 to 30 days apart). The presence of active malignancy is indicated if, in the two subject samples (aliquots) obtained at different times with the period between times at least 5 days, the parameter of probe binding to serum albumin is within a control range (or near a representative control value for the range) exhibited by serum albumin in control subjects with active malignancies or outside a control range (or a representative control value for the range) exhibited by serum albumin in healthy control subjects without cancer, and if the subject patient did not have indications of acute diseases occur during the period between the times at which the two samples were obtained. In some embodiments (e.g., those in which the values calculated for the subject patient are compared to one or more control values for health patients), the change in probe binding parameter can be normalized to account for the reduction in serum albumin concentration, such that the normalized probe binding parameter can be compared directly to the control range. The control subjects may be any one subject or group of subjects suitable for comparison, including, for example, one or more cancer-free patients, chronic disease subjects, healthy subjects, or the like.

Investigations of solutions of serum albumin have revealed that the binding constant Kb (which may also be known in the art as the inverse of the dissociation constant or as the ratio of the association and dissociation coefficients) of albumin in hydrophilic solution, e.g. serum, with respect to hydrophobic substances (e.g., binding of long chain fatty acids to serum albumin), can be reduced by the addition of a solvent (e.g., alcohol), as illustrated by the linear function of the inverse of solvent concentration:

$$Kb = K \cdot (Sc/S - 1) \qquad (1)$$

where Kb is the binding constant, S is the solvent concentration, Sc is the critical concentration of the solvent in a solution at which the probe is completely soluble (will completely dissociate from the serum albumin and dissolve in the solution), and K is the constant equal to binding constant Kb in a solution containing the solvent at concentration of Sc/2. One possible explanation for this is that hydrophobic forces in hydrophilic solutions are functions of the entropy and the enthalpy of the solution, and the introduction of such solvents can modify each of the entropy and the enthalpy of the solution, in some instances, for example, as a linear function of solvent concentration.

Without the addition of solvent to the aliquot, other factors such as, for example, concentrations of various metabolites and serum proteins, temperature, pH variations, and the like, can influence the entropy of the water medium and cause significant variations in the hydrophobic forces in the aliquot. This can result in variations in the concentration of the unbound (free) fraction of the hydrophobic probe. In contrast, the addition of an amount of solvent that increases the concentration of unbound probe in the mixture (of aliquot, probe, and solvent) to at least 5 times greater than the concentration of unbound probe before the addition of the solvent (e.g., a mixture with only the aliquot and probe) can overcome the influence of stochastic factors on the aliquot, and thereby significantly reduce variations in measured results down, for example, to 20% or less.

Concentrations of specific site-bound, non-specific site-bound, and unbound (free) fractions of the probe, and other fractions, can be measured by any suitable methods or techniques. For example, the concentrations of the probe bound on specific and non-specific hydrophobic sites of serum albumin and unbound (free) fractions of the labeled probe in the mixture of the aliquot, probe, and solvent can be measured by: fluorescence spectroscopy of dichroism (e.g., where the probe has a fluorescent label), EPR-spectroscopy (e.g., where the probe has a spin label), or the like. However, without the addition of polar solvent at a relatively low concentration in the aliquot, the concentration of unbound-free probe in the aliquot may be below a minimal concentration measurable with such methods of measurements. Some embodiments of the present methods include mixing a solvent with the aliquot, where the amount (volume, concentration, or the like) is such that the solvent does not induce significant conformational changes to albumin in the aliquot and/or significant dissociation of albumin-bound metabolites. In some embodiments, the amount of solvent is such that the concentration of unbound probe in the mixture is increased to a level sufficient for accurate measurement by the method of measurement used. For example, in some embodiments, the amount of solvent mixed with the aliquot is the smallest amount necessary to increase the concentration of unbound probe in a mixture of probe, aliquot, and solvent to at least about five times greater than the concentration of unbound probe in a mixture of only the same probe and aliquot.

Some embodiments of the present method can include one or more intermediate or preparation steps for preparing the mixture after mixing the aliquot, probe, and solvent but before measuring the concentrations of albumin-bound and unbound (free) fractions of the probe. For example, for probes having fluorescent labels, the mixture can be incubated in a dialysis tube divided into two volumes by a membrane that is permeable to the probe but not permeable to serum proteins in the mixture so as to separate the mixture into two portions, a first portion containing serum proteins and unbound probe, and a second portion containing unbound probe but substantially no serum proteins. By repeating the dialysis procedure described above for the portion containing serum proteins with an appropriate membrane, a sub-portion containing serum albumin can be isolated. After incubation, the probe concentration can be measured for each of the serum-albumin-containing and serum-protein-free portions of the mixture.

Measurement of the concentrations of protein-bound probe and/or unbound probe depends of the type of labeled probe used. The first separated portion (with serum proteins and unbound probe) and/or isolated sub-portion (with serum albumin) can be analyzed using measurement of fluorescence or circuit dichroism fluorescence. If the measurement method is unsuitable for direct measurement of free probe (e.g., spectroscopy of some fluorescent labels), the second separated portion can be mixed with a portion of albumin and the concentration of the previously-unbound probe analyzed similar to the portion of albumin-bound probe as it is described above.

By way of another example, for a spin-labeled probe, the mixture can be analyzed using an EPR-spectrometer to obtain an EPR spectrum of the probe such that the EPR spectrum is simultaneously indicative of different spectral components corresponding to albumin-bound, unbound (free) and other fractions of the probe in the mixture. More specifically, spectral analysis of the EPR-spectrum can permit separation of single spectral components, identification of their relation to different binding sites of serum albumin and unbound fractions of spin probe, and approximation or estimation of their relative concentrations. Deep analysis of spectral parameters of single spectral components can permit an approximation or estimation of detailed probe binding parameters characterizing a mobility of a spin-labeled probe bound on the hydrophobic sites of serum albumin, such as, for example, polarity of an albumin site surrounding a bound probe molecule, freedom (degree of ordering) of the probe molecule, and a correlation time of their rotation or oscillation. Taken together, these parameters can permit detailed analysis of conformational changes occurred to albumin molecule under binding of ligands. Examples of commercially-available software for simulating and/or analyzing EPR spectra include: EasySpin, a MATLAB toolbox for simulating and fitting Electron Paramagnetic Resonance (EPR) spectra (available from www.easyspin.org); EPR Spectra Simulation of Anisotropic Spin 1/2 System (available from Hanging Wu, Department of Chemistry, University of Wisconsin-Milwaukee); ACERT programs (available from the Department of Chemistry and Chemical Biology of Cornell University); EPR Software Suites (available from Bruker Biospin); The EPR Spectral Simulation Program (available from The Hoffman Group at Northwestern University); and Public Electron Paramagnetic Resonance Software Tools (available from the National Institute of Environmental Health Sciences—National Institute of Health).

Taken separately, parameters of relative concentrations of a probe bound on specific sites of serum albumin, probe bound on non-specific sites of serum albumin, and unbound probe, can permit approximation or estimation of binding efficiencies (BE) and/or BE-parameters characterizing an affinity of these albumin sites. Binding efficiency (BE) of a type of albumin site (e.g., specific sites or non-specific sites) is the concentration ratio of probe bound to the respective type of site (e.g., specific sites) and probe not bound to the respective type of site (e.g., probe bound to non-specific sites, unbound probe, probe aggregated into micelles, and probe bound to lipoproteins). In some embodiments of the present methods, binding efficiency is derived, calculated, or otherwise determined once the mixture of aliquot, probe, and solvent has reached binding equilibrium (with respect to the binding of probe to carrier proteins). For serum albumin, which has relatively high allosteric interactions of binding sites, the binding efficiency parameters themselves can permit approximation or estimation of a conformational change or modification to albumin due to change of a content of albumin-bound metabolites occurring, for example, in the circulatory system of patients with active malignancy.

In some embodiments of the present methods, the mixture of aliquot, probe, and solvent (e.g., after incubation but before analyzing), permitted to reach binding equilibrium and/or is tested to determine whether binding equilibrium has been reached. Testing for binding equilibrium may be useful, for example, in instances in which the aliquot of serum has a relatively higher viscosity that may require a longer period of incubation to reach binding equilibrium (e.g., the state at which substantially all probe that will bind to albumin—whether limited by the amount of the probe or by the available capacity of the albumin—has actually bound to the albumin). For example, serum samples from patients with renal impairment, plasmacytosis, macroglobulinemia may have increased viscosity that can decrease the speed of probe diffusion, and thereby increase the time required to reach binding equilibrium. In some embodiments, whether the mixture has reached binding equilibrium is tested by measuring two EPR spectra (e.g., via a capillary comprising a portion of the mixture) of the mixture at two different times (e.g., separated by, for example, 1, 2, 3, 4, 5, 10, 15, or more minutes), and analyzing the EPR spectra for identity or correspondence of spectral parameters or intensities of spectral lines derived from each spectrum. If the two spectra are substantially the same, then binding equilibrium is likely to have been reached. One example of a technique for the comparison of two spectra for this purpose is a curve fitting by the method of least squares (regression), followed by a t-test of the regression parameters. If the t-test indicates that the two EPR spectra are distinct or different, then the mixture may be incubated for an additional period of time (e.g., 5, 10, 15, or more minutes) and may be re-tested to verify binding equilibrium after that additional incubation period. In some instances, if binding equilibrium cannot be verified initially or after additional incubation, the mixture may be excluded as defective. If the t-test indicates that the two EPR spectra have no significant difference, this indicates that the reaction of a probe binding to serum albumin in the mixture reached equilibrium. If binding equilibrium has been reached, the measured EPR spectra used for verifying binding equilibrium may also be used for analyzing one or more parameters of probe binding to sites of serum albumin in the sample.

At the condition of binding equilibrium in the mixture of sample aliquot, probe, and solvent, the binding efficiencies (BE1 and BE2) of specific (primary) and non-specific (secondary) hydrophobic binding sites of serum albumin can be calculated using the concentrations of the probe bound on the primary site of albumin (B1), on the secondary albumin site (B2) and unbound probe concentration (F), and solvent concentration (S) in the mixture. For example, can be calculated with either:

$$1/BE1 = 1/(Kb1 \cdot N1) = (Sc/S - 1) \cdot (F/B1) \cdot P \cdot (1 - B1/(P \cdot N1)) \quad (2)$$

$$1/BE2 = 1/(Kb2 \cdot N2) = (Sc/S - 1) \cdot (F/B2) \cdot P \cdot (1 - B2/(P \cdot N2)) \quad (3)$$

where $Sc = 0.27$ volume percent is the critical concentration of the solvent (as described above), P is the concentration of serum albumin in the sample, N1 is the number of specific or primary binding sites for the probe on the serum albumin molecule, N2 is the number of non-specific or secondary binding sites for the probe between the albumin on the serum albumin molecule. Generally, where the probe is a long chain fatty acid, $N1 = 7$ and N2 is from 6 to 8 for purified albumin. For native serum albumin of a healthy person N1 is from 4 to 7, and N2 is from 3 to 7. In native serum samples, typically the relative concentration of the spin probe bound on primary site, parameter B1/P, is about 0.5; and parameter B2/P is about 0.4. Therefore, the binding efficiencies BE1 and BE2 can be calculated (within about 10%) using the approximate formulas:

$$1/BE1 = (Sc/S - 1) \cdot (F/B1) \cdot P \quad (2a)$$

$$1/BE2 = (Sc/S - 1) \cdot (F/B2) \cdot P \quad (3a)$$

If two aliquots of a sample are analyzed with different concentrations of spin probe or solvent (e.g., ethanol) concentration, the equations (2) and (3) can be solved precisely as a set of linear equations, that will give precise estimation of parameters BE1 and N1 from equation (2) and BE2 and N2 from equation (3).

The present methods were performed for cancer-free control patients and patients with active malignancy to determine control values of probe binding parameters for cancer-free patients, including control values such as mean and a range of normal variation, and to determine control values for cancer patients with active malignancies. For example, Table 1 demonstrates the data on difference of probe binding parameters and their derivatives determined in the performed investigation.

TABLE 1

Parameters of spin probe 16-doxyl stearic acid binding to primary and secondary binding sites of serum albumin obtained in the investigation of 93 cancer-free persons and 95 patients with active malignancies[1]

| Group of patients | | Parameters of probe binding to serum albumin | | | | | |
|---|---|---|---|---|---|---|---|
| | | B1 | B2 | F | B1/F | B2/F | DP |
| Cancer-free persons n = 95 | Mean | 0.52 | 0.38 | 0.026 | 21.8 | 15.8 | −3.3 |
| | Min | 0.40 | 0.34 | 0.010 | 10.4 | 8.5 | −5.2 |
| | Max | 0.60 | 0.45 | 0.044 | 54.4 | 37.5 | −0.3 |
| | SD | 0.04 | 0.03 | 0.008 | 8.3 | 5.3 | 0.9 |
| | CV | 8% | 7% | 30% | 38% | 34% | 27% |
| Patients with active malignancies n = 104 (17 colon cancer, 18 breast cancer, 50 prostate cancer, 19 lung cancer) | Mean | 0.44 | 0.33 | 0.079 | 5.9 | 4.5 | 8.0 |
| | Min | 0.32 | 0.23 | 0.047 | 2.3 | 1.6 | 0.1 |
| | Max | 0.54 | 0.38 | 0.155 | 11.4 | 6.5 | 66.0 |
| | SD | 0.04 | 0.03 | 0.018 | 1.5 | 1.1 | 11.5 |
| | CV | 9% | 10% | 23% | 25% | 24% | 144% |

[1]Reagent concentrations in the measured mixtures were: serum albumin concentration of 0.47 mmol, spin probe concentration of 1.64 mmol, ethanol concentration of 0.22 volume percent.

In Table 2, B1 and B2 are relative concentrations of the probe bound on primary and secondary sites of albumin, F is the relative concentration of unbound probe, B1/F and B2/F are parameters representing the binding efficiency of the primary and secondary binding sites of albumin, DP is discriminating parameter designed by square discriminant analysis using a set of probe binding parameters.

As will be understood by those of ordinary skill in the art, discriminant analysis generally refers to a method of classification or pattern recognition in which a computer sorts or identifies combinations of groups of values for variables, with each group including values that are relatively close to one another and relatively distinct or farther apart from values in other groups. The combinations are generally referred to as discriminant functions, which are also referred to as classifiers, and allow recognition of complex patterns, to distinguish between exemplars based on their different patterns, and to make predictions on their classification. A discriminant function can be a linear combination of the discriminating variables (linear discriminant function) or quadratic combination (quadratic discriminant function). Quadratic discriminant analysis is the most commonly used method for deriving a classifier from empirical data or databases for two or more classes of variables.

The presented data confirm that the parameters of the spin probe binding to primary and secondary hydrophobic sites of albumin reveal changes to albumin molecules in patients with active malignancies. In the patients with active malignancies the concentration of the probe bound on primary albumin sites, parameter B1, was reduced by 0.08 compared to healthy subjects; and the relative concentration of free or unbound probe molecules, parameter F, was increased by 0.053 compared to healthy subjects. There the most significant difference between the cancer-free persons and the patients with active malignancies was observed for parameter B2/F, e.g. binding efficiency of the probe on the secondary albumin site in accordance with equation (3) described above. Other parameters of the probe binding to the albumin site also indicated that there is an allosteric modification of the hydrophobic sites of albumin in the circulatory system of patients with active malignancies. For example, the parameter B2/F can be used as the discriminant parameter for detection of the allosteric change of hydrophobic sites of serum albumin conformation and diagnostics of an active malignancy in the subject patient. By use of quadratic discriminant analysis of the data observed for control groups of cancer-free persons and patients with active malignancies, the probe binding parameters can be combined in one probe binding parameter or discriminant parameter DP, in such a way that changes of conformation and binding efficiencies of the both hydrophobic sites of serum albumin become a most distinguishable.

Using quadratic discriminant analysis, a discriminant parameter DP can be calculated using the matrix algebra with the formula:

$$DP = 0.5 \cdot \{(x-\mu_1)[M_1]^{-i}(x-\mu_1) - (x-\mu_2)[M_2]^{-i}(x-\mu_2) + \ln(\det[M_1]) - \ln(\det[M_2])\}$$

where x=(B1,B2,F) is vector of three probe binding parameters, $\mu_1$ is vector of mean values and $M_1$ is covariation matrix of these parameters for the group of cancer-free persons, $$\mu_1 = (0.499, 0.373, 0.04),$$

$$M_1 = \begin{bmatrix} 0.00172 & -0.00077 & -0.00024 \\ -0.00077 & 0.00076 & -0.0001 \\ -0.00024 & -0.0001 & 0.00018 \end{bmatrix},$$

$\mu_2$ is vector of mean values and M2 is covariation matrix of these parameters for the group of patients with active malignancies, $$\mu_2 = (0.439, 0.334, 0.077),$$

$$M_2 = \begin{bmatrix} 0.00216 & 0.00016 & -0.00062 \\ 0.00016 & 0.00139 & -0.0005 \\ -0.00062 & -0.0005 & 0.00043 \end{bmatrix}.$$

Accuracy of a discriminant parameter, for example B2/F and/or DP, generally depends on precise approximation of parameters of the probe binding on serum albumin sites. Investigations performed with the described method revealed that in the mixtures prepared using a serum or plasma aliquots, there can be between 0% to 20% (e.g., 0% to 10%) of the hydrophobic probe (e.g., 16-doxyl stearic acid) aggregated into micelles, and between 0% to 10% (e.g., 0% to 10%) of the probe bound on lipoproteins. Portions of probe micelles and/or lipoprotein-bound probe present in the analyzed mixture can cause inaccurate approximation or estimation of probe binding parameters of albumin that leads to increased number of false-negative and false-positive diagnoses of active malignancies. In the present methods, and in contrast to U.S. Pat. No. 7,166,474 (described above in background section), the step of analyzing the mixture (aliquot, probe, and solvent) can comprise excluding of a portion of the probe bound on lipoproteins and a portion of the probe aggregated into micelles before or simultaneously with analyzing the portions of albumin-bound and unbound probe. For example, EPR spectra for lipoproteins may be similar to EPR spectra for unbound probe, and EPR spectra for micelles may be similar to EPR spectra for albumin-bound probe, which may in some instances undermine the precision of the measured ratio of bound and unbound probe. As such, in some embodiments, it can be beneficial to analytically remove or separate EPR spectra for lipoproteins and micelles to more-precisely measure the bound and unbound portions of probe. In other embodiments (e.g., in which fluorescent probe is used), lipoproteins and micelles may be physically removed via one or more filters, membranes, or the like.

In the present methods, and in contrast to U.S. Pat. No. 7,166,474 (described above), the presence of active malignancy can be indicated if in a first subject sample obtained from a subject patient's extracellular fluid, one or more parameters (e.g., the probe binding parameter) is closer to one or more control parameters (e.g., the binding parameter(s)) of one or more control patients with an active malignancy than to the binding parameters of the cancer-free control patients. The presence of active malignancy can be further indicated and/or confirmed if in a second subject sample obtained from a subject patient's extracellular fluid between 2 and 30 days after the first subject sample was obtained, the one or more parameters are closer to the one or more control parameters (e.g., and if the subject patient had no indication of acute diseases occurring during the period between the times at which the respective samples were obtained). Whether a subject had an indication of acute disease occurring during the period between the samples can be determined by observing and/or asking the patient. The one or more control parameters may be calculated for a healthy person (e.g., a healthy person that is related to the patient) or multiple healthy persons, may be aggregated or averaged from multiple healthy persons, and/or may include one or more values or ranges expected for healthy persons.

The use of two samples obtained at different times can reduce false-positive indications of active malignancy (e.g., that may be indicated by the first sample in subject patients with asymptomatic development of acute infection or disease at the time of the first sample), by confirming the lack or absence of symptoms during the period between samples and analyzing the second sample to confirm the results of analyzing the first sample. For example, during the stage of asymptomatic development of an acute infection or disease (often 2 to 5 days) the subject patient can have elevated levels of toxins and acute-phase metabolites in the circulatory system. Serum albumin, as the main carrier protein in serum, binds such metabolites and delivers them to liver for cleaning in hepatocytes and removal by liver. Therefore, in a subject patient with asymptomatic development of an infection or disease, measured parameters of the serum albumin can be changed by the binding of toxins and acute-phase metabolites, and can result in false-positives during analysis of the first sample in the present methods. During the time period of 5 to 30 days, symptoms of the acute infection or disease of a subject patient will generally appear, and what could have been a false-positive indication from the first aliquot can be avoided. For example, such a subject patient can be re-examined after recovery (e.g., 20 to 30 days after symptoms of the acute infection or disease have ceased). Due to the life time period of serum albumin in the circulatory system of about 20 days, a portion of serum albumin molecules with bound toxins and acute-phase metabolites will be cleaned in hepatocytes or replaced by new albumin molecules synthesized by liver in the subject patient.

Some embodiments of the present methods can comprise testing blood, plasma, plasma products and/or albumin solutions prior to injection or infusion of such plasma products or albumin solutions into a patient. Some embodiments of the present methods can comprise evaluating or monitoring a patient's response to tumor resection, chemotherapy, X-ray therapy, and/or other therapies or treatments. Some embodiments of the present methods can comprise testing or evaluating the health of a subject patient to assess the patient's readiness or suitability for a task, assignment, and/or deployment, such as, for example, submarine duty, military deployment, specific line of employment, and/or specific tasks or group of tasks.

Some embodiments of the present methods can comprise evaluating the viability of donor organs (e.g., liver, kidney, or the like) by testing a sample of the donor's blood serum or other extracellular fluid. Some embodiments of the present methods may comprise evaluating blood (e.g., donated blood) for the presence of cancer-associated metabolites and/or the like.

Example of EPR Spectroscopy

Some embodiments of the present methods can use EPR spectroscopy to analyze the mixture of aliquot, probe, and solvent (some of which probe is generally bound to albumin in the mixture). One example of a suitable labeled probe is depicted in FIG. 4, which depicts a suitably labeled stearic acid molecule, 16-doxyl stearic acid. The mixture can be placed into the EPR spectrometer and exposed to both a high magnetic field and microwave power, and various properties (such as the properties described herein) of the mixture measured (directly or indirectly).

1. Binding of Spin-Labeled Probe to Serum Albumin in the Sample

Figure 1A:
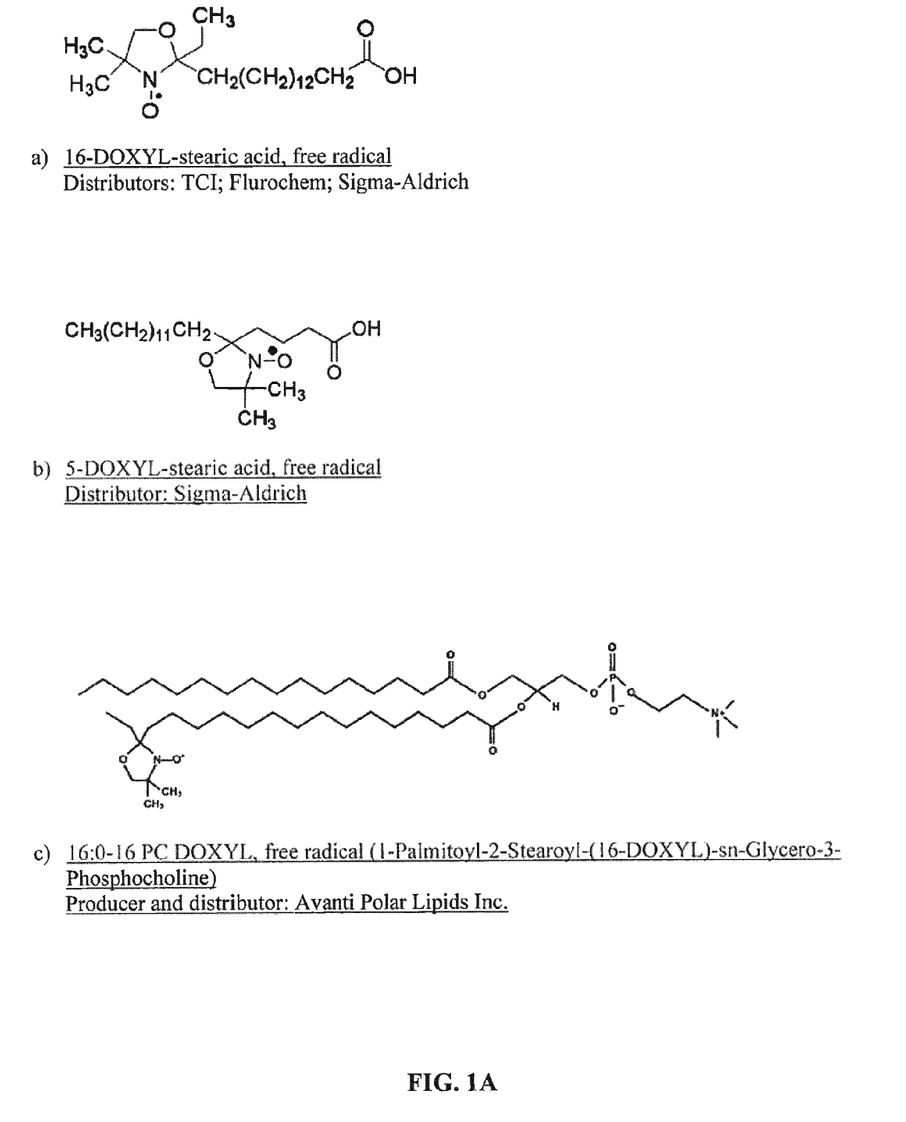
FIGS. 1A-1B depict graphical representations of a number of labeled probes for use in various embodiments of the present methods.
Figure 1B:
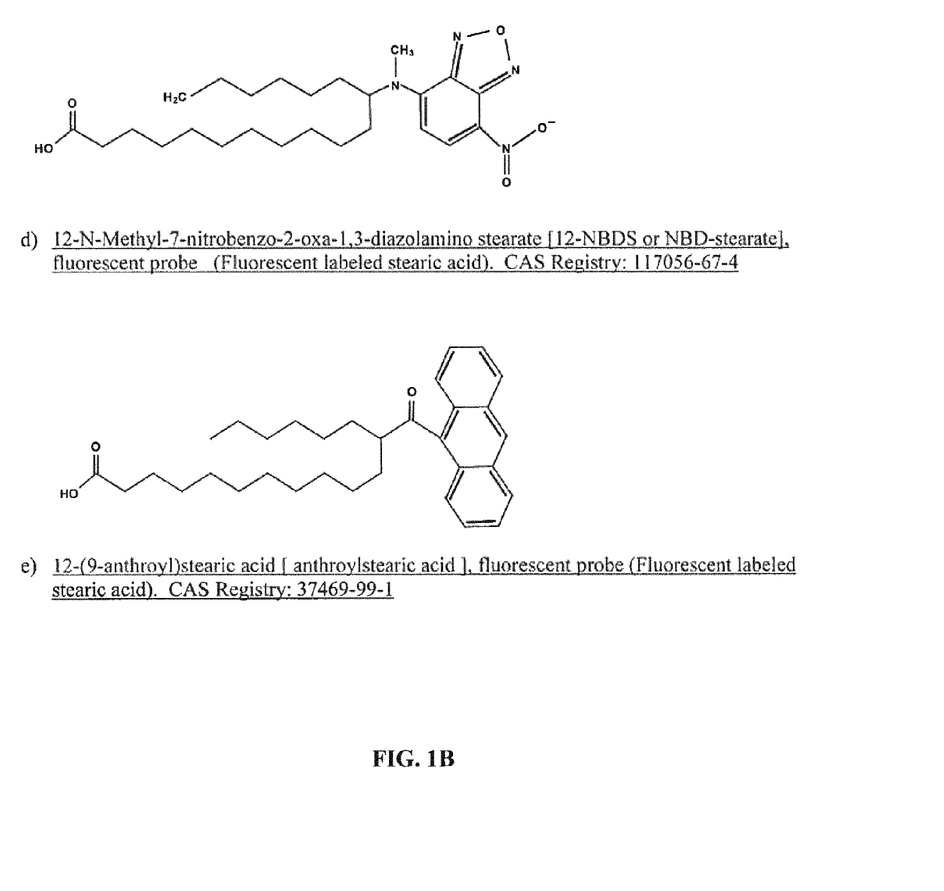

Spin-labeled fatty acid probes (e.g., as shown in FIG. 1A-1B) can be used to study serum albumin by EPR spectroscopy. Spin-labeled fatty acid probes may also be referred to herein as "fatty acid probes" (and more generally "labeled probes" or "probes"). One exemplary procedure includes mixing an amount of labeled fatty acid probe (e.g. 16-doxyl stearic acid, a fatty acid labeled with a nitroxide radical) with a small (i.e., 50 µl) amount of serum or plasma. The molar ratio of the probe to serum albumin can be in the range between about 3 and about 5 so as to, for example, permit a level of binding that is sufficient to be representative of the binding ability of the specific (e.g., long-chain fatty acids) and non-specific (e.g., metabolites) hydrophobic sites of serum albumin in the subject patient's body at the time the sample was taken from the subject patient while preventing saturation of the fatty acid binding sites on the serum albumin. Capacity of the albumin's specific binding site for long chain fatty acid is known to be about 7 (e.g., up to seven long chain fatty acid molecules can be bound at a specific albumin site), and the capacity of the non-specific hydrophobic site of serum albumin is higher (e.g., up to more than seven long chain fatty acid molecules can be bound at a non-specific albumin site). The labeled probe can also be mixed with a polar solvent such as, for example, ethanol. The binding affinity of specific and non-specific hydrophobic sites of serum albumin for the labeled probe can be reduced by the ethanol to increase the number of unbound probe molecules in the mixture, as described above. After mixing the probe and solvent with the aliquot of serum, the resultant mixture can be incubated with constant agitation (e.g., at 5-8 Hz) for 10 min at 37° C. or for 20 min at room temperature (e.g., 20-25° C.).

Figure 2:
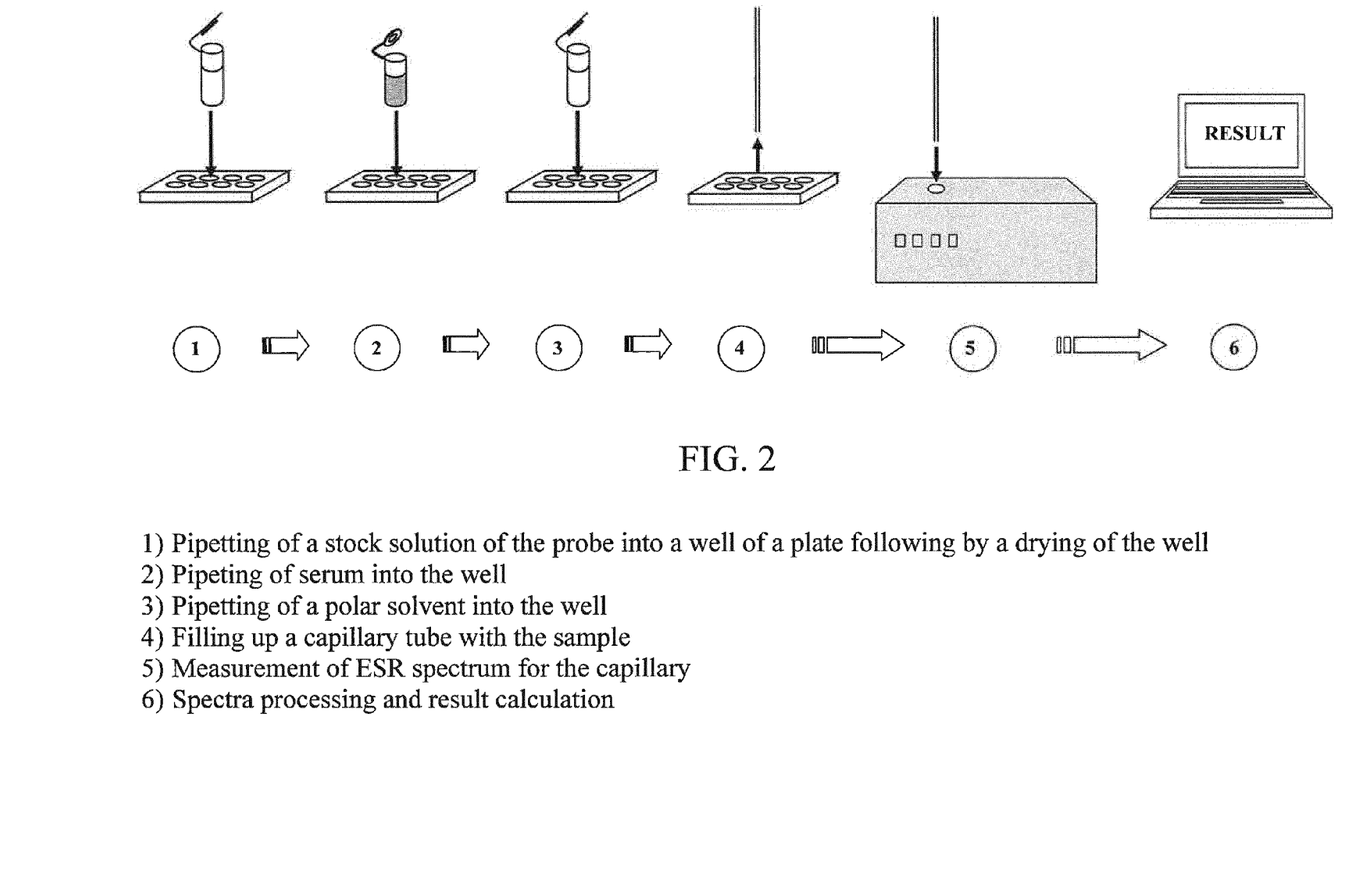
FIG. 2 depicts a schematic representation of one exemplary procedure for evaluating a mixture containing an aliquot of serum and an amount of labeled probe by EPR spectroscopy that is suitable for use in embodiments of the present methods.

This exemplary procedure is schematically depicted in FIG. 2. The embodiment of the present methods depicted in FIG. 2 includes: (1) placing the probe into a container, (2) mixing an aliquot of serum with the probe in the container, (3) mixing solvent with the aliquot and probe in the container, (4) placing the mixture (of aliquot, probe, and solvent) into a pipette (before or after incubation), (5) placing the pipette into, and analyzing the mixture with, the EPR spectrometer to obtain EPR spectra of the mixture, and (6)

processing the measurements to obtain the concentrations of protein-bound and unbound probe, and determining the parameters of probe binding to hydrophobic sites of serum albumin in the serum of the aliquot. The steps and/or order of steps depicted and/or described in this embodiment of the present methods are not intended to be limiting. Other embodiments of the present methods may omit any of these steps, and/or may include other steps, may include any combination of these or other steps in any suitable order.

The affinity of albumin for 16-doxyl stearic acid (the labeled probe) may generally be similar to its affinity for unlabeled stearic acid (which may be relatively high, e.g., a binding constant of about $10^9$ mol$^{-1}$). In blood serum of a healthy patient (and in the absence of binding site saturation), the abundance of albumin relative to other serum proteins and the presence of several high-affinity binding sites for long chain fatty acids may result in 99% or more of the stearic acid probe being bound exclusively to albumin.

2. Instrumentation

Following incubation of the probe with the sample, an amount of the mixture can be placed into a glass capillary tube. The tube can then be inserted into an EPR spectrometer (e.g., Model No. EPR 01-08 available from MedInnovation GmbH, Wildau, Germany, or Model No. AXM-09 available from Scientific Production Enterprise Albutran, Minsk, Belarus). In the EPR spectrometer, the mixture is exposed to both a high magnetic field and microwave power. This exposure induces resonance of the spin label and absorption of microwave power. An EPR spectrum can thereby be generated by scanning measurements of the magnetic field strength and absorption of microwave power. Other EPR spectrometers, such as conventional X-Band EPR spectrometers, or other EPR spectrometers operating with a microwave frequency of approximately 9-10 GHz, can be also used for obtaining these measurements. The sample can be maintained at 37° C. during the measurement process to mimic physiologic conditions.

3. Data Processing

The EPR spectrum obtained with the spin probe can be analyzed using a simulation process. Simulation can be performed using least-square fitting of a model spectrum to the measured spectrum. In this way, the EPR spectrum of the spin probe can be calculated using the appropriate model and parameters of the site where the spin probe is situated.

The EPR spectrum obtained will generally consists of a large set of data points containing some amount of measurement noise or error. If the parameters of the binding site model are accurately established, an ideal experimental spectral curve can generally be derived. This task may be more complex when there are several sites that can bind the spin probe. In this situation, these different binding sites can be considered to improve accuracy when deriving the model spectrum. A number of different tools have been developed that enable the derivation of a composite model spectrum for compounds that possess several binding sites for the spin probe.

Figure 3:
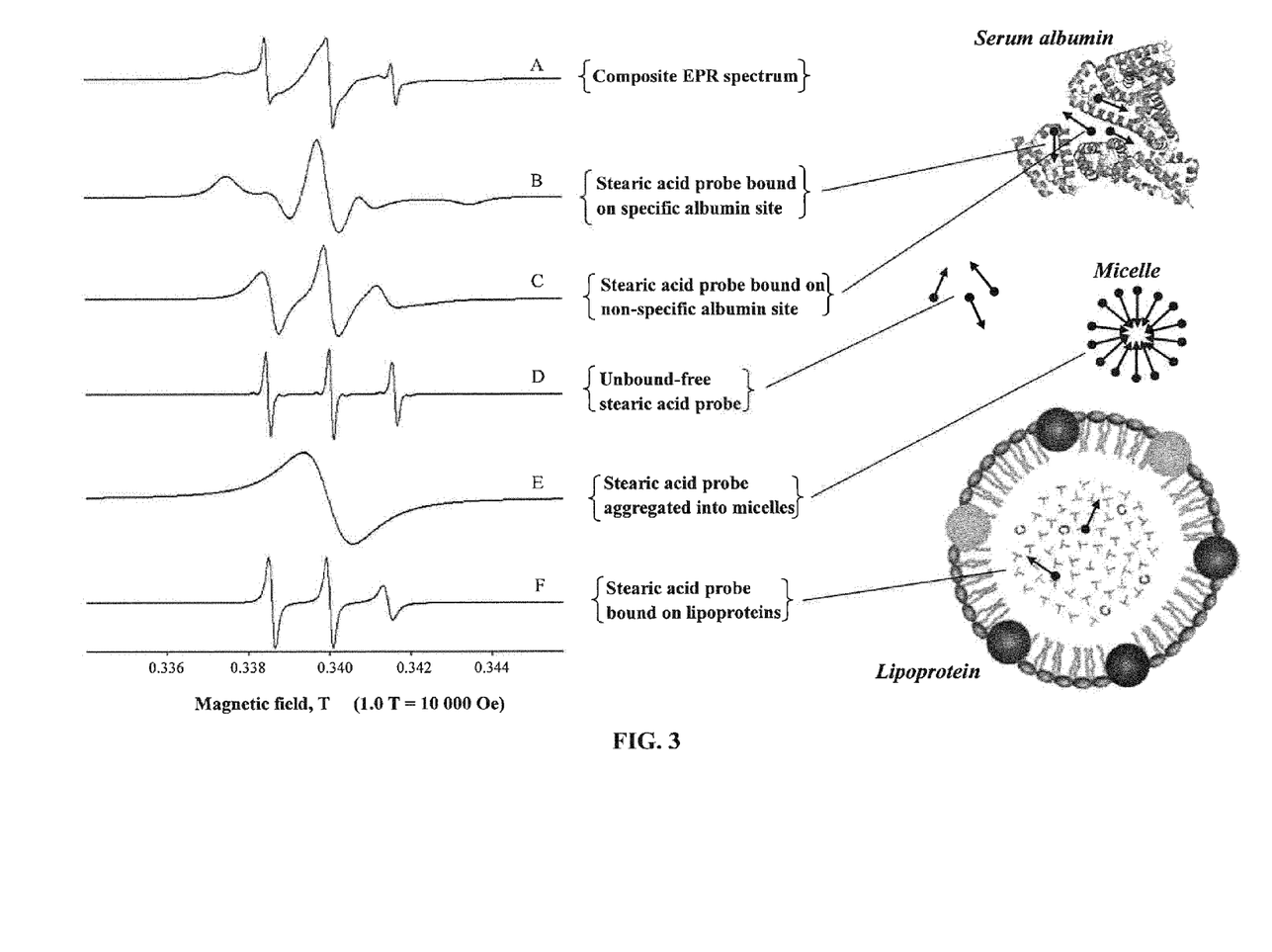
FIG. 3 depicts an exemplary EPR spectrum of a mixture of serum and a spin-labeled fatty acid probe (16-doxyl stearic acid) obtained by an EPR spectroscopy method of analysis that is suitable for use in embodiments of the present methods.

Analysis of the EPR spectrum generated from the stearic acid probe bound to albumin (as described above) reveals five distinct spectral components. The major portion of the spectrum is represented by two components, as represented by lines B and C in FIG. 3. Each of these two spectra components (B and C) is representative of the respective portions of fatty acid probe bound to the specific and non-specific hydrophobic sites of serum albumin (as may correspond to the pictorial representation of serum albumin molecules). The three remaining components (D, E, F), respectively, are representative of: unbound probe molecules present singularly in solution, as represented by line D in FIG. 3 (as may correspond to the pictorial representation of individual, unbound probe molecules); probe aggregated into clusters of fatty acid micelles, as represented by line E in FIG. 3; and probe associated with or bound to lipoproteins, as represented by line F in FIG. 3. The process of simulation generally determines the values of ideal spectrum parameters representing the equation that provides the best curve fit of the simulated and measured spectra. These parameters can include the intensity of each spectral component as well as specific EPR parameters determining the position, width, and shape of spectrum lines.

Each EPR spectrum reflects the structural and functional characteristics of the albumin that impact the binding of the probe to the specific (also referred to in some literature as "primary"), and the non-specific (also referred to in some literature as "secondary") sites of serum albumin. One technique that is employed for the generation of EPR spectra includes a sample mixture (of serum aliquot, probe, and solvent). The characteristics of the probe binding to albumin can be assessed from the EPR spectra resulting from the respective portions or concentrations of the fatty acid probe bound to specific and non-specific albumin sites, and the portion or concentration of unbound probe. Another characteristic that can be generated is an estimation of changes in albumin conformation (significant conformational changes are prevented and/or minimized in the present methods) at the albumin binding sites for fatty acids (certain parameters of the EPR spectrum indicate the mobility of the fatty acid probe at its binding sites on albumin); such mobility can be influenced by several parameters, and those parameters can be used to detect an absence or presence of significant conformational changes of albumin molecule due to albumin binding of toxins, acute-phase metabolites, and/or excessive concentration of a polar solvent in a sample mixture).

Exemplary Data Obtained Through Testing of the Present Methods

The present methods have been tested on cancer-patients suffering from active malignancies and on healthy subjects. The common methods employed in this testing are discussed first, and the results of this testing on several specific cases are discussed below. The samples tested were obtained at the Blokhin Russian Oncological Scientific Center of the Russian Academy of Medical Science, Moscow, Russia, and the N.N. Alexandrov National Cancer Centre of Belarus for Oncology and Medical Radiology, Minsk, Belarus.

These samples were then frozen at −30° C. (minus 30° C.), and later investigated by the inventor of the present methods.

Blood serum was obtained by whole blood centrifugation. An aliquot of 50 μl of serum from each patient was used for each test. A spin probe of 2-(14-carboxytetradecyl)-2-ethyl-4,4-dimethyl-3-oxazolidinyloxy (purchased from Fluorochem Ltd., Derbyshire, UK) was mixed into the aliquot at a concentration of 1.64 mmol/l. A solvent, 14 μl of ethanol, was mixed into the aliquot. The molar ratio of the probe to serum albumin in the aliquot was 3.5, based on an albumin concentration in the serum of 4 g/dL. The mixture was then incubated for 10 min at 37° C. with continuous agitation in a standard shaker operated at about 5-8 Hz.

After incubation, the probe was placed into a glass capillary (e.g., Model No. RM-40, available from KABE LABORTECHNIK GmbH, Numbrecht-Elsenroth, Germany).

The EPR spectrum of the mixture was then measured, as described below. The above-described capillary was placed into the resonator of an EPR spectrometer for spectroscopic analysis. The spectroscopy parameters were as follows: microwave power 15 mW at frequency 9.52 GHz; magnetic field 0.34 T (3400 G) with scan range 12 mT (120 G); modulation amplitude 0.2 mT (2 G); data accumulation by three scans each with 4096 measured points and a sweep time 60 s. The capillary temperature was 37° C., and was controlled within +/−0.2° C.

The EPR spectrum was analyzed by computer using an EPR-spectrum simulation with nonlinear least-squares fits. The spectrum model included five components. The first two are the B and C components which represent portions of the probe that were bound differently on serum albumin. As shown here, the B and C components primarily differed by spectral parameters of A tensors (hyperfine splitting tensor): $A\|(B)=30.02$ Oe, $A\perp(B)=9.02$ Oe, $A\|(C)=21.5$ Oe, and $A\perp(C)=13.35$ Oe. Parameters of the g tensor used in the spectral calculations of these two components were: $g\|(B)=1.9983$, $g\perp(B)=2.0019$, $g\|(C)=1.9990$, and $g\perp(C)=2.0013$. The third D component represented the unbound spin probe residing free in the sample. The parameters of the D component were: $A\|(D)=A\perp(D)=15.6$ Oe, and $g\|(D)=g\perp(D)=2.0008$. The width of spectrum line for the D component, $L(D)=0.42$ Oe, was significantly different from the width of the spectrum line for the B and C components, $L(B)=L(C)=3.45$ Oe. The fourth and fifth components represented fractions of the probe that were not related to albumin-bound or unbound-free probe, but to the probe molecules aggregated into micelles (E) and ones associated with lipoproteins (F). The parameters of the E component were: $A\|(E)=A\perp(E)=0$, $g\|(E)=g\perp(E)=2.0014$, and $L(E)=11.96$ Oe. The parameters of the F component were: $A\|(F)=A\perp(F)=14.2$ Oe, $g\|(F)=g\perp(F)=2.0012$, and $L(F)=1.1$ Oe. The considering of the E and F components in the spectrum model can improve accuracy of the analysis of concentrations of albumin-bound and unbound-free probes, but is not necessarily required in embodiments of the present methods.

During the EPR-spectrum simulation with nonlinear least-squares fits, relative concentrations of all spectral components as well as precise values of spectral parameters were determined. At the specified ethanol concentration, the majority of the (spin) probe, i.e., about 90 to 95%, was found to be bound on serum albumin. The unbound fraction of the spin probe was found to have a relative concentration of 0.5 to 10% (e.g., 3 to 8%), and was found to vary somewhat among samples of different patients, and among different samples taken under different clinical conditions (clinical statuses) of the same patient.

(A) Patient with Colon Cancer

Patient A was diagnosed with a tumor of colon. The first sample was obtained at the time of Patient A entered the oncology clinic for colonoscopy. Relative concentration of probe micelles and lipoprotein-bound probe in the analyzed sample aliquot, parameter LM, was 13.8%. Probe binding parameter B2/F was determined to be reduced down to 5.1 compared the normal range of from 8.5 to 37.5, and parameter DP was increased to 2.1 compared the normal range of from −5.2 to −0.3. The second sample was derived after the time period of 12 days. The probe binding parameters were determines to be: LM of 13.6%, B2/F of 5.4 and DP of 2.1. The presence of the active malignant colon tumor was confirmed by biopsy.

(B) Patient with Colon Cancer

Patient B was diagnosed with cancer of sigmoid colon. In the first sample, relative LM was 15.1%, parameter B2/F was 4.6, and DP was increased to 5.5. The second sample was derived after a period of 14 days. The second sample parameters were: LM of 16.7%, B2/F of 3.3, and DP of 12.5. The sigmoid colon cancer was confirmed by biopsy.

(C) Patient with Prostate Cancer

Patient C was diagnosed with aggressive prostate cancer. In the first sample, LM was 15.8%, parameter B2/F was 3.1, and DP was increased to 10.0. The patient's PSA was increased to 24.0. The second sample was derived after the time period of 14 days. The second sample parameters were: LM of 16%, B2/F of 5.2, and DP of 11.8. The aggressive prostate cancer was confirmed by biopsy.

(D) Patient with Breast Cancer

Patient D was diagnosed with breast cancer. In the first sample, LM was 14.8%, B2/F was 4.6, and DP was 4.2. The second sample was taken after 14 days. In the second sample LM was 15.7%, B2/F was 5.1, and DP was 4.3. The presence of breast tumor was confirmed by biopsy.

(E) Healthy Person

Volunteer E was observed to be without evidence of any diseases. In the obtained sample parameter LM was 6.9%, B2/F was 18.1, and DP was −3.2. The parameters were in the normal ranges for cancer-free persons.

(F) Healthy Person

Volunteer F observed to be without evidence of any diseases. In the obtained sample, LM was 3.5%, B2/F was 21.1, and DP was −4.0. The parameters were in the normal ranges for cancer-free persons.

(G) Cancer-Free Patient Who Had Assimpomatic Development of Acute Disease

Patient G suffered from acute respiratory disease during the period between the times of the obtaining of first and second samples. In the first sample, LM was 11.1%, B2/F was 5.3 (in the range of from 1.6 to 6.5 observed for patients with active malignancies), and DP was 0.4 (in range of 0.1 to 66 observed in cancer patients). The second sample was derived 28 days later. In the second sample, LM was 8.6%, B2/F was 9.0, and DP was −1.9. The parameters in the second sample were in the normal ranges for cancer-free persons.

Some embodiments of the invention include a kit including materials for performing the various steps of the invention. In one exemplary embodiment of a kit for detecting active malignancy in a subject patient from a sample of the subject patient's serum, the kit includes an amount of labeled probe and an amount of solvent. The amounts of probe and solvent are such that when mixed with aliquot of serum having about a predetermined volume (e.g., 50, 60, 70, 80, 90, 100, or more μL), the mixture will achieve the results described above, and/or have the proportions of ingredients described above.

In other embodiments, the kit can include components for performing the various steps and/or portions of the present methods, as described herein. In some embodiments, the kit can further include instructions for performing the various steps or portions of the present methods, as described above.

In any of the various embodiments described or suggested in this disclosure, the methods can comprise or be limited to any combination of the steps, features, and/or characteristics that have been described, unless the context explicitly or necessarily precludes the combination. For example, one embodiment of the present method can include mixing probe with an aliquot and measuring the concentrations of albumin-bound and unbound probe; and another embodiment can include mixing probe and solvent with the aliquot, measuring the concentrations of albumin-bound and unbound probe, and normalizing the concentrations to substantially negate the changes in concentrations caused by the addition of the solvent. By way of another example, one embodiment of the present kits can include a pipette and an amount of probe; another embodiment can include an amount of probe and an amount of solvent; and another embodiment can include an amount of probe, an amount of liquid solution, and an amount of solvent.

The various illustrative embodiments of methods and kits described herein are not intended to be limited to the particular forms disclosed. Rather, they include all modifications, equivalents, and alternatives falling within the scope of the claims. For example, embodiments of the present methods can include measuring (e.g., indirectly) the concentrations of albumin-bound and unbound probe in a mixture (aliquot, probe, solvent) with EPR spectroscopy, fluorescent spectroscopy, or any other suitable methods described or otherwise known or developed in the art.

The claims are not intended to include, and should not be interpreted to include, means-plus- or step-plus-function limitations, unless such a limitation is explicitly recited in a given claim using the phrase(s) "means for" or "step for," respectively.

REFERENCES

D. J. Schneider and J. H. Freed, *Calculating Slow Motional Magnetic Resonance Spectra: A User's Guide*, Spin Labeling: Theory and Applications, Vol. III, *Biological Magnetic Resonance* 8, 1-76 (1989)

The invention claimed is:

1. A method for detecting active malignancy in a subject patient, comprising:
   mixing a labeled hydrophobic probe capable of binding to specific and non-specific hydrophobic binding sites of serum albumin with an aliquot of a first sample of a subject patient's serum albumin-containing extracellular fluid, the amount of probe such that the molar ratio of the probe to the serum albumin is between 2 and 7, the probe optionally comprising two or more substances;
   mixing a solvent with the aliquot of the first sample, the solvent such that when added to the aliquot and probe the solubility of the probe is increased in the aliquot, and the amount of solvent is sufficient to dissociate a portion of the probe from the serum albumin without causing significant dissociation of hydrophobic metabolites from the serum albumin, the solvent optionally comprising two or more substances;
   analyzing the mixture of aliquot, probe, and solvent to determine for the first sample one or more binding parameters of the probe, where analyzing the mixture comprises:
      substantially excluding from the mixture a portion of the probe that is bound on lipoproteins and a portion of the probe that is aggregated into micelles; and
      determining the one or more probe binding parameters of the sample from the remaining portion of the probe in the mixture; and
   comparing the one or more binding parameters of the first sample to one or more control binding parameters of a probe binding to serum albumin in the extracellular fluid of at least one of: a cancer-free control patient and a control patient with an active malignancy.

2. The method of claim 1, further comprising:
   mixing a labeled hydrophobic probe capable of binding to specific and non-specific hydrophobic binding sites of serum albumin with an aliquot of a second sample of the subject patient's serum albumin-containing extracellular fluid taken from the subject patient between 2 and 90 days after the first sample, the amount of probe such that the molar ratio of the probe to the serum albumin is between 2 and 7, the probe optionally comprising two or more substances;
   mixing a solvent with the aliquot of the second sample, the solvent such that when added to the aliquot and probe the solubility of the probe is increased in the aliquot, and the amount of solvent is sufficient to dissociate a portion of the probe from the serum albumin without causing significant dissociation of hydrophobic metabolites from the serum albumin, the solvent optionally comprising two or more substances;
   analyzing the mixture of aliquot, probe, and solvent to determine for the second sample one or more binding parameters of the probe, where analyzing the mixture comprises:
      substantially excluding from the mixture a portion of the probe that is bound on lipoproteins and a portion of the probe that is aggregated into micelles; and
      determining the one or more probe binding parameters of the sample from the remaining portion of the probe in the mixture; and
   comparing the one or more binding parameters of the second sample to one or more control binding parameters of a probe binding to serum albumin in the extracellular fluid of at least one of: a cancer-free control patient and a control patient with an active malignancy.

3. The method of claim 2, further comprising:
   diagnosing an active malignancy in the subject patient if:
      (i) the one or more binding parameters for each of the two samples are closer to the one or more control binding parameters for the at least one control patient with an active malignancy than to the one or more control binding parameters of the cancer-free control patient, and
      (ii) the subject patient had no indication of acute disease or infection that occurred between the times of the deriving of the samples.

4. The method of claim 2, where the one or more probe binding parameters of each sample are determined from the portion of the probe bound to specific and non-specific hydrophobic binding sites of albumin, and the portion of unbound probe.

5. The method of claim 2, where the two samples are taken from the subject patient between 5 and 90 days apart, between 2 and 30 days apart, or between 5 and 30 days apart.

6. The method of claim 2, further comprising:
   verifying that the subject patient had no indication of acute diseases that occurred between the times at which the two samples were taken from the patient.

7. The method of claim 2, where analyzing each mixture comprises:
   measuring the concentrations of the probe bound on specific and non-specific hydrophobic sites of serum albumin, and the unbound probe in the mixture; and
   deriving the one or more probe binding parameters from at least the concentrations of: the probe bound to specific and non-specific hydrophobic binding sites of albumin, and the unbound probe.

8. The method of claim 2, where the probe comprises an organic molecule having between 8 and 28 Carbon atoms, and optionally, where the probe comprises one or more of: a fatty acid, a long-chain fatty acid, 16-DOXYL-stearic acid, or a lysophospholipid.

9. The method of claim 2, where the amount of solvent mixed with the aliquot and probe is such that the solvent does not induce significant conformational changes of albumin.

10. The method of claim 2, where the amount of solvent mixed with the aliquot and probe is sufficient to increase the concentration of unbound probe in the mixture of the aliquot, the probe, and the solvent to at least 5 times greater than the concentration of unbound probe in a mixture of the aliquot and the probe without the solvent.

11. The method of claim 2, where the volume of the solvent mixed with the aliquot is less than 30% of the volume of the aliquot, and optionally less than 20% of the volume of the aliquot.

12. The method of claim 2, further comprising:
normalizing the one or more probe binding parameters of each sample to account for the reduction in albumin concentration caused by the solvent in the mixture;
optionally, where the steps of deriving and normalizing the one or more probe binding parameters are performed simultaneously.

13. The method claim 2, further comprising:
normalizing the one or more probe binding parameters of each sample to account for the reduction in serum albumin concentration caused by medical conditions of the patient.

14. The method claim 2, where the one or more control parameters comprise at least one range of control parameters of control patients.

15. The method of claim 7, further comprising:
repeating the steps of mixing a probe, mixing a solvent, measuring the concentrations, deriving a one or more probe binding parameters for each of two or more aliquots, where a different amount of solvent is used for each of the two or more repetitions; optionally, where the one or more probe binding parameters derived for the two or more repetitions are averaged to derive an average probe binding parameters, and where the averaged one or more probe binding parameters are compared in the step of comparing the one or more probe binding parameters.

16. The method of claim 2, where the volume of the aliquot is less than 100 µL, and optionally, less than 50 µL.

17. The method of claim 2, where the probe is labeled with a spin-label.

18. The method of claim 2, where the extracellular fluid includes at least one of: blood serum, blood plasma, lymph fluid, and spinal fluid.

19. The method of claim 2, where analyzing each mixture comprises verifying that the mixture has reached binding equilibrium, optionally by:
measuring two EPR spectra of the mixture at two different times;
comparing the two EPR spectra to determine whether intensities of spectral lines (spectral parameters) in the EPR spectra correspond.

\* \* \* \* \*